(12) United States Patent
Tanwar

(10) Patent No.: US 11,994,513 B2
(45) Date of Patent: May 28, 2024

(54) DIAGNOSTIC AND PROGNOSTIC METHODS FOR ESTROGEN-INDUCED CANCERS

(71) Applicant: The University of Newcastle, Callaghan (AU)

(72) Inventor: Pradeep S. Tanwar, Callaghan (AU)

(73) Assignee: The University of Newcastle, Callaghan (AU)

( * ) Notice: Subject to any disclaimer, the term of this patent is extended or adjusted under 35 U.S.C. 154(b) by 628 days.

(21) Appl. No.: 17/041,981

(22) PCT Filed: Mar. 29, 2019

(86) PCT No.: PCT/AU2019/050281
§ 371 (c)(1),
(2) Date: Sep. 25, 2020

(87) PCT Pub. No.: WO2019/183683
PCT Pub. Date: Oct. 3, 2019

(65) Prior Publication Data
US 2021/0025872 A1    Jan. 28, 2021

(30) Foreign Application Priority Data

Mar. 29, 2018  (AU) ................................ 2018901055

(51) Int. Cl.
G01N 33/50    (2006.01)
(52) U.S. Cl.
CPC ... *G01N 33/5091* (2013.01); *G01N 2333/916* (2013.01); *G01N 2496/00* (2013.01); *G01N 2800/7028* (2013.01)
(58) Field of Classification Search
CPC ......... G01N 33/5091; G01N 2333/916; G01N 2496/00; G01N 2800/7028
See application file for complete search history.

(56) References Cited

U.S. PATENT DOCUMENTS

| | | | | |
|---|---|---|---|---|
| 2003/0008299 | A1* | 1/2003 | Algate | C07K 14/47 435/325 |
| 2008/0193454 | A1* | 8/2008 | Tureci | C07K 16/30 435/320.1 |
| 2018/0369409 | A1* | 12/2018 | Liu | A61K 47/6811 |

FOREIGN PATENT DOCUMENTS

| WO | WO 2010/040446 A1 | 4/2010 |
|---|---|---|
| WO | WO 2017/095823 A1 | 6/2017 |

OTHER PUBLICATIONS

Fishman, W. H., "Clinical and Biological Significance of an Isozyme Tumor Marker—PLAP", Clin. Biochem, 1987, vol. 20, pp. 387-392, See whole document especially p. 388.
Liu, S. et al., "High expression of ALPPL2 is associated with poor prognosis in gastric cancer", Human Pathology, 2019, vol. 86, pp. 49-56, See whole document especially p. 50.
Stendahl, U. et al., "Expression of Placental Alkaline Phosphatase in Epithelial Ovarian Tumours", Tumor Biol, 1989, vol. 10, pp. 126-132, See whole document especially p. 126.
Stigbrand, T. et al., "Placental Alkaline Phosphatase (PLAP)/PLAP-like alkaline phosphatase as tumour marker in relation to CA 125 and TPA for ovarian epithelial tumours", Eur. J. Gynaec. Oncol., 1990, vol. 11, No. 5, pp. 351-360.
International Search Report for PCT/AU2019/050281 dated Jun. 6, 2019.
Johnson, Suzanne M. et al., "Ishikawa cells exhibit differential gene expression profiles in response to oestradiol or 4-hydroxytamoxifen" Endocrine-Related Cancer, 2007, pp. 337-350, vol. 14.
Qinan, Yin "A human in vitro study to identify the effects of estrogenic-like and (anti)progestin-like chemicals on endometrial biomarkers" Medicine and Health Sciences, Chinese Doctoral Dissertations Full-text Database, No. 2, E068-3, May 2013.
Office Action for CN 201980036301.0 issued Sep. 2, 2023.

* cited by examiner

*Primary Examiner* — Changhwa J Cheu
(74) *Attorney, Agent, or Firm* — Knobbe Martens Olson & Bear LLP

(57) ABSTRACT

Provided herein are methods for detecting an estrogen-induced cancer in a subject, for identifying a subject at risk of developing an estrogen-induced cancer and for determining or predicting prognosis for a subject with an estrogen-induced cancer. The methods of the disclosure comprise determining the level of expression of ALPPL2 in a biological sample, typically a blood sample, obtained from a subject.

12 Claims, 5 Drawing Sheets

Specification includes a Sequence Listing.

SEQUENCE LISTING

<160> NUMBER OF SEQ ID NOS: 11

<210> SEQ ID NO 1
<211> LENGTH: 532
<212> TYPE: PRT
<213> ORGANISM: Homo sapiens

<400> SEQUENCE: 1

Met Gln Gly Pro Trp Val Leu Leu Leu Gly Leu Arg Leu Gln Leu
1               5                   10                  15

Ser Leu Gly Ile Ile Pro Val Glu Glu Asn Pro Asp Phe Trp Asn
            20                  25                  30

Arg Gln Ala Ala Glu Ala Leu Gly Ala Ala Lys Lys Leu Gln Pro Ala
        35                  40                  45

Gln Thr Ala Ala Lys Asn Leu Ile Ile Phe Leu Gly Asp Gly Met Gly
    50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
            100                 105                 110

Ala Thr Ala Thr Ala Tyr Leu Cys Gly Val Lys Gly Asn Phe Gln Thr
        115                 120                 125

```
Ile Gly Leu Ser Ala Ala Ala Arg Phe Asn Gln Cys Asn Thr Thr Arg
    130                 135                 140

Gly Asn Glu Val Ile Ser Val Met Asn Arg Ala Lys Lys Ala Gly Lys
145                 150                 155                 160

Ser Val Gly Val Val Thr Thr Thr Arg Val Gln His Ala Ser Pro Ala
                    165                 170                 175

Gly Ala Tyr Ala His Thr Val Asn Arg Asn Trp Tyr Ser Asp Ala Asp
                180                 185                 190

Val Pro Ala Ser Ala Arg Gln Glu Gly Cys Gln Asp Ile Ala Thr Gln
            195                 200                 205

Leu Ile Ser Asn Met Asp Ile Asp Val Ile Leu Gly Gly Arg Lys
    210                 215                 220

Tyr Met Phe Pro Met Gly Thr Pro Asp Pro Glu Tyr Pro Asp Tyr
225                 230                 235                 240

Ser Gln Gly Gly Thr Arg Leu Asp Gly Lys Asn Leu Val Gln Glu Trp
                    245                 250                 255

Leu Ala Lys His Gln Gly Ala Arg Tyr Val Trp Asn Arg Thr Glu Leu
                260                 265                 270

Leu Gln Ala Ser Leu Asp Pro Ser Val Thr His Leu Met Gly Leu Phe
            275                 280                 285

Glu Pro Gly Asp Met Lys Tyr Glu Ile His Arg Asp Ser Thr Leu Asp
    290                 295                 300

Pro Ser Leu Met Glu Met Thr Glu Ala Ala Leu Leu Leu Ser Arg
305                 310                 315                 320

Asn Pro Arg Gly Phe Phe Leu Phe Val Glu Gly Gly Arg Ile Asp His
                    325                 330                 335

Gly His His Glu Ser Arg Ala Tyr Arg Ala Leu Thr Glu Thr Ile Met
                340                 345                 350

Phe Asp Asp Ala Ile Glu Arg Ala Gly Gln Leu Thr Ser Glu Glu Asp
            355                 360                 365

Thr Leu Ser Leu Val Thr Ala Asp His Ser His Val Phe Ser Phe Gly
    370                 375                 380

Gly Tyr Pro Leu Arg Gly Ser Ser Ile Phe Gly Leu Ala Pro Gly Lys
385                 390                 395                 400

Ala Arg Asp Arg Lys Ala Tyr Thr Val Leu Leu Tyr Gly Asn Gly Pro
                    405                 410                 415

Gly Tyr Val Leu Lys Asp Gly Ala Arg Pro Asp Val Thr Glu Ser Glu
                420                 425                 430

Ser Gly Ser Pro Glu Tyr Arg Gln Gln Ser Ala Val Pro Leu Asp Gly
            435                 440                 445

Glu Thr His Ala Gly Glu Asp Val Ala Val Phe Ala Arg Gly Pro Gln
    450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
                    485                 490                 495

Pro Arg Ala Gly Thr Thr Asp Ala Ala His Pro Gly Pro Ser Val Val
                500                 505                 510

Pro Ala Leu Leu Pro Leu Leu Ala Gly Thr Leu Leu Leu Gly Thr
            515                 520                 525

Ala Thr Ala Pro
            530
```

```
<210> SEQ ID NO 2
<211> LENGTH: 513
<212> TYPE: PRT
<213> ORGANISM: Homo sapiens

<400> SEQUENCE: 2
```

| | | | | | | | | | | | | | | | |
|---|---|---|---|---|---|---|---|---|---|---|---|---|---|---|---|
| Ile | Ile | Pro | Val | Glu | Glu | Glu | Asn | Pro | Asp | Phe | Trp | Asn | Arg | Gln | Ala |
| 1 | | | | 5 | | | | | 10 | | | | | 15 | |
| Ala | Glu | Ala | Leu | Gly | Ala | Ala | Lys | Lys | Leu | Gln | Pro | Ala | Gln | Thr | Ala |
| | | | 20 | | | | | 25 | | | | | 30 | | |
| Ala | Lys | Asn | Leu | Ile | Ile | Phe | Leu | Gly | Asp | Gly | Met | Gly | Val | Ser | Thr |
| | | | 35 | | | | 40 | | | | | 45 | | | |
| Val | Thr | Ala | Ala | Arg | Ile | Leu | Lys | Gly | Gln | Lys | Lys | Asp | Lys | Leu | Gly |
| | 50 | | | | | 55 | | | | | 60 | | | | |
| Pro | Glu | Thr | Phe | Leu | Ala | Met | Asp | Arg | Phe | Pro | Tyr | Val | Ala | Leu | Ser |
| 65 | | | | 70 | | | | | 75 | | | | | 80 | |
| Lys | Thr | Tyr | Ser | Val | Asp | Lys | His | Val | Pro | Asp | Ser | Gly | Ala | Thr | Ala |
| | | | | 85 | | | | | 90 | | | | | 95 | |
| Thr | Ala | Tyr | Leu | Cys | Gly | Val | Lys | Gly | Asn | Phe | Gln | Thr | Ile | Gly | Leu |
| | | | 100 | | | | | 105 | | | | | 110 | | |
| Ser | Ala | Ala | Ala | Arg | Phe | Asn | Gln | Cys | Asn | Thr | Thr | Arg | Gly | Asn | Glu |
| | | | 115 | | | | | 120 | | | | | 125 | | |
| Val | Ile | Ser | Val | Met | Asn | Arg | Ala | Lys | Lys | Ala | Gly | Lys | Ser | Val | Gly |
| | 130 | | | | | 135 | | | | | 140 | | | | |
| Val | Val | Thr | Thr | Thr | Arg | Val | Gln | His | Ala | Ser | Pro | Ala | Gly | Ala | Tyr |
| 145 | | | | | 150 | | | | | 155 | | | | | 160 |
| Ala | His | Thr | Val | Asn | Arg | Asn | Trp | Tyr | Ser | Asp | Ala | Asp | Val | Pro | Ala |
| | | | | 165 | | | | | 170 | | | | | 175 | |
| Ser | Ala | Arg | Gln | Glu | Gly | Cys | Gln | Asp | Ile | Ala | Thr | Gln | Leu | Ile | Ser |
| | | | 180 | | | | | 185 | | | | | 190 | | |
| Asn | Met | Asp | Ile | Asp | Val | Ile | Leu | Gly | Gly | Gly | Arg | Lys | Tyr | Met | Phe |
| | | | 195 | | | | | 200 | | | | | 205 | | |
| Pro | Met | Gly | Thr | Pro | Asp | Pro | Glu | Tyr | Pro | Asp | Asp | Tyr | Ser | Gln | Gly |
| | 210 | | | | | 215 | | | | | 220 | | | | |
| Gly | Thr | Arg | Leu | Asp | Gly | Lys | Asn | Leu | Val | Gln | Glu | Trp | Leu | Ala | Lys |
| 225 | | | | | 230 | | | | | 235 | | | | | 240 |
| His | Gln | Gly | Ala | Arg | Tyr | Val | Trp | Asn | Arg | Thr | Glu | Leu | Leu | Gln | Ala |
| | | | | 245 | | | | | 250 | | | | | 255 | |
| Ser | Leu | Asp | Pro | Ser | Val | Thr | His | Leu | Met | Gly | Leu | Phe | Glu | Pro | Gly |
| | | | 260 | | | | | 265 | | | | | 270 | | |
| Asp | Met | Lys | Tyr | Glu | Ile | His | Arg | Asp | Ser | Thr | Leu | Asp | Pro | Ser | Leu |
| | | | 275 | | | | | 280 | | | | | 285 | | |
| Met | Glu | Met | Thr | Glu | Ala | Ala | Leu | Leu | Leu | Leu | Ser | Arg | Asn | Pro | Arg |
| | 290 | | | | | 295 | | | | | 300 | | | | |
| Gly | Phe | Phe | Leu | Phe | Val | Glu | Gly | Gly | Arg | Ile | Asp | His | Gly | His | His |
| 305 | | | | | 310 | | | | | 315 | | | | | 320 |
| Glu | Ser | Arg | Ala | Tyr | Arg | Ala | Leu | Thr | Glu | Thr | Ile | Met | Phe | Asp | Asp |
| | | | | 325 | | | | | 330 | | | | | 335 | |
| Ala | Ile | Glu | Arg | Ala | Gly | Gln | Leu | Thr | Ser | Glu | Glu | Asp | Thr | Leu | Ser |
| | | | 340 | | | | | 345 | | | | | 350 | | |
| Leu | Val | Thr | Ala | Asp | His | Ser | His | Val | Phe | Ser | Phe | Gly | Gly | Tyr | Pro |
| | | | 355 | | | | | 360 | | | | | 365 | | |
| Leu | Arg | Gly | Ser | Ser | Ile | Phe | Gly | Leu | Ala | Pro | Gly | Lys | Ala | Arg | Asp |
| | 370 | | | | | 375 | | | | | 380 | | | | |

```
Arg Lys Ala Tyr Thr Val Leu Leu Tyr Gly Asn Gly Pro Gly Tyr Val
385                 390                 395                 400

Leu Lys Asp Gly Ala Arg Pro Asp Val Thr Glu Ser Glu Ser Gly Ser
            405                 410                 415

Pro Glu Tyr Arg Gln Gln Ser Ala Val Pro Leu Asp Gly Glu Thr His
            420                 425                 430

Ala Gly Glu Asp Val Ala Val Phe Ala Arg Gly Pro Gln Ala His Leu
            435                 440                 445

Val His Gly Val Gln Glu Gln Thr Phe Ile Ala His Val Met Ala Phe
        450                 455                 460

Ala Ala Cys Leu Glu Pro Tyr Thr Ala Cys Asp Leu Ala Pro Arg Ala
465                 470                 475                 480

Gly Thr Thr Asp Ala Ala His Pro Gly Pro Ser Val Val Pro Ala Leu
            485                 490                 495

Leu Pro Leu Leu Ala Gly Thr Leu Leu Leu Gly Thr Ala Thr Ala
                500                 505                 510

Pro
```

<210> SEQ ID NO 3
<211> LENGTH: 1599
<212> TYPE: DNA
<213> ORGANISM: Homo sapiens

<400> SEQUENCE: 3

```
atgcagggc cctgggtgct gctcctgctg ggcctgaggc tacagctctc cctgggcatc      60
atcccagttg aggaggagaa cccggacttc tggaaccgcc aggcagccga ggccctgggt     120
gccgccaaga agctgcagcc tgcacagaca gccgccaaga acctcatcat cttcctgggt     180
gacgggatgg gggtgtctac ggtgacagct gccaggatcc taaagggca gaagaaggac      240
aaactggggc tgagacctt cctggccatg accgcttcc gtacgtggc tctgtccaag        300
acatacagtg tagacaagca gtgccagac agtggagcca cagccacggc ctacctgtgc      360
ggggtcaagg gcaacttcca gaccattggc ttgagtgcag ccgcccgctt taaccagtgc     420
aacacgacac gcggcaacga ggtcatctcc gtgatgaatc gggccaagaa agcaggaaag     480
tcagtgggag tggtaaccac cacgggtg cagcatgcct cgccagccgg cgcctacgcc        540
cacacggtga accgcaactg gtactcggat gccgacgtgc ctgcctcggc ccgccaggag      600
gggtgccagg acatcgccac gcagctcatc tccaacatgg acattgatgt gatcctaggt     660
ggaggccgaa agtacatgtt tcccatgggg accccagacc tgagtaccc agatgactac      720
agccaaggtg ggaccaggct ggacgggaag aatctggtgc aggaatggct ggcgaagcac     780
cagggtgccc ggtacgtgtg aaccgcact gagctcctgc aggcttccct ggacccgtct      840
gtgacccatc tcatgggtct ctttgagcct ggagacatga atacgagat ccaccgagac      900
tccacactgg acccctccct gatggagatg acagaggctg ccctgctcct gctgagcagg     960
aacccccgcg gcttcttcct cttcgtggag ggtggtcgca tcgaccatgg tcatcatgaa    1020
agcagggctt accgggcact gactgagacg atcatgttcg acgacgccat tgagagggcg    1080
ggccagctca ccagcgagga ggacacgctg agcctcgtca ctgccgacca ctcccacgtc    1140
ttctcccttcg gaggctaccc cctgcgaggg agctccatct tcgggctggc ccctggcaag    1200
gcccgggaca ggaaggccta cacggtcctc tatacggaa acggtccagg ctatgtgctc     1260
aaggacggcg cccggccga tgttacggag agcgagagcg ggagcccga gtatcggcag      1320
cagtcagcag tgcccctgga cggagagacc cacgcaggcg aggacgtggc ggtgttcgcg    1380
```

```
cgcggcccgc aggcgcacct ggttcacggc gtgcaggagc agaccttcat agcgcacgtc   1440
atggccttcg ccgcctgcct ggagccctac accgcctgcg acctggcgcc ccgcgccggc   1500
accaccgacg ccgcgcaccc ggggccgtcc gtggtccccg cgttgcttcc tctgctggca   1560
gggaccttgc tgctgctggg gacggccact gctccctga                          1599
```

<210> SEQ ID NO 4
<211> LENGTH: 19
<212> TYPE: DNA
<213> ORGANISM: Homo sapiens

<400> SEQUENCE: 4

```
tgttaccgag agcgagagc                                                19
```

<210> SEQ ID NO 5
<211> LENGTH: 18
<212> TYPE: DNA
<213> ORGANISM: Homo sapiens

<400> SEQUENCE: 5

```
gtgggtctct ccgtccag                                                 18
```

<210> SEQ ID NO 6
<211> LENGTH: 20
<212> TYPE: DNA
<213> ORGANISM: Mus musculus

<400> SEQUENCE: 6

```
acacatggct ctgtccaaga                                               20
```

<210> SEQ ID NO 7
<211> LENGTH: 20
<212> TYPE: DNA
<213> ORGANISM: Mus musculus

<400> SEQUENCE: 7

```
tcgtgttgca ctggttgaag                                               20
```

<210> SEQ ID NO 8
<211> LENGTH: 21
<212> TYPE: DNA
<213> ORGANISM: Homo sapiens

<400> SEQUENCE: 8

```
gccacatcgc tcagacacca t                                             21
```

<210> SEQ ID NO 9
<211> LENGTH: 20
<212> TYPE: DNA
<213> ORGANISM: Homo sapiens

<400> SEQUENCE: 9

```
gaagggtca ttgatggcaa                                                20
```

<210> SEQ ID NO 10
<211> LENGTH: 22
<212> TYPE: DNA
<213> ORGANISM: Mus musculus

<400> SEQUENCE: 10

```
tggcaaagtg gagattgttg cc                                            22
```

-continued

```
<210> SEQ ID NO 11
<211> LENGTH: 21
<212> TYPE: DNA
<213> ORGANISM: Mus musculus

<400> SEQUENCE: 11
aagatggtga tgggcttccc g                                              21
```

DIAGNOSTIC AND PROGNOSTIC METHODS FOR ESTROGEN-INDUCED CANCERS

CROSS REFERENCE TO RELATED APPLICATIONS

This application is a U.S. National Phase Application of PCT International Application Number PCT/AU2019/050281, filed on Mar. 29, 2019, designating the United States of America and published in the English language, which is an International Application of and claims the benefit of priority to Australian Patent Application No. 2018901055, filed on Mar. 29, 2018. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-DAVI557-002APC.txt, the date of creation of the ASCII text file is Sep. 25, 2020, and the size of the ASCII text file is 12.2 KB.

TECHNICAL FIELD

The present disclosure relates generally to methods and protocols for the diagnosis and prognosis of estrogen-induced cancers, in particular endometrial cancer and ovarian cancer.

BACKGROUND OF THE DISCLOSURE

Uterine (endometrial) cancer is the fifth most common gynecological cancer worldwide, with over 60,000 new cases diagnosed and nearly 10,000 deaths every year. The overall 5-year survival of endometrial cancer patients without metastasis ranges from 74% to 91%. However, in case of women with stage IV endometrial cancer, the long-term survival rate drops to 20%. Obesity is an independent risk factor and approximately 50% of cases are associated with high body mass index (BMI, >30 kg/m$^2$).

Endometrial cancer is most common in post-menopausal women. Early menarche and late menopause, or a long duration of estrogen exposure, can lead to a prolonged growth of endometrium followed by endometrial hyperplasia and cancer. Hypertrophied adipocytes in obese women are a predominant source of the enzyme aromatase, which synthesizes excess in situ estrogen and promotes endometrial adenocarcinomas. Therefore, an elevated level of estrogen is strongly associated with susceptibility to endometrial cancer.

Standard treatment for the majority of endometrial cancer patients is major surgery, typically hysterectomy or bilateral salpingo-oophorectomy (fallopian tube and ovary removal). However the five year survival rate for endometrial cancer patients is poor due to the fact the cancer is most often only diagnosed when at an advanced stage.

There is a clear need for the identification of biomarkers for early detection of the disease, making earlier treatment possible. Early diagnosis can make a significant difference to patient prognosis. If endometrial cancer is diagnosed at stage I or II, five year survival rates are approximately 90%. However if the cancer is not diagnosed until it has reached stage III or IV, the five year survival rate drops dramatically to only about 40%. The majority of endometrial cancer patients (~90%) have endometrioid histology, which is significantly associated with a hyperestrogenic state. Thus, identification of estrogen-responsive biomarkers would be of particular benefit in earlier detection of elevated estrogen levels and endometrial cancer diagnosis.

There is currently no universally approved biomarker for endometrial cancer. High levels of the oncoprotein stathmin have been shown to be associated with aggressive endometrial cancer and poor prognosis, however the use of stathmin as a biomarker is limited to patients with advanced stages of endometrial cancer. A blood test may be used pre-operatively in endometrial cancer patients to determine CA-125 levels, however the usefulness of CA-125 as a biomarker for endometrial cancer is limited by lack of specificity and sensitivity, lack of ability to detect early stage cancer and poor prognostic power.

There remains a need for biomarkers of endometrial and related cancers with improved diagnostic and prognostic power.

SUMMARY OF THE DISCLOSURE

In one aspect, the present disclosure provides a method for detecting an estrogen-induced cancer in a subject, the method comprising executing the steps of:
 (a) determining the level of expression of placental-like alkaline phosphatase 2 (ALPPL2) in a biological sample obtained from the subject; and
 (b) comparing the determined level of expression to the level of expression of ALPPL2 in one or more estrogen-induced cancer-free reference samples,
wherein an elevated level of expression of ALPPL2 in the sample obtained from the subject relative to that in one or more reference samples is indicative of the presence of estrogen-induced cancer in the subject.

Determining the level of expression of ALPPL2 may comprise a qualitative or quantitative determination of expression of an ALPPL2 protein. Alternatively, determining the level of expression of ALPPL2 may comprise a qualitative or quantitative determination of expression of ALPPL2 mRNA.

The determination of ALPPL2 expression levels may be subjected to one or more statistical analyses. Exemplary statistical analyses include, but are not limited to, receiver operator characteristic (ROC) analysis, logistic regression analysis, Spearman's rank correlation analysis, and the Mann-Whitney U test. In an exemplary embodiment, the method comprises determining a statistical value derived from the level of expression of the ALPPL2 from the sample obtained from the subject and the one or more reference samples and comparing said statistical values. The comparing step may comprise, for example, ROC analysis.

The estrogen-induced cancer may be, for example, endometrial cancer, ovarian cancer or breast cancer. In exemplary embodiments the estrogen-induced cancer is endometrial cancer or ovarian cancer.

In exemplary embodiments the biological sample obtained from the subject is a fluid sample, more typically a blood sample, such as a whole blood, blood plasma or serum sample. Typically the reference sample(s) is a fluid sample, more typically a blood sample, such as a whole blood, blood plasma or serum sample. The reference sample(s) may be derived from one or more individuals known not to have estrogen-induced cancer.

In another aspect, the present disclosure provides a method for identifying a subject at risk of developing an estrogen-induced cancer, the method comprising the steps of:
- (a) determining the level of expression of ALPPL2 in a biological sample obtained from the subject; and
- (b) comparing the determined level of expression to the level of expression of ALPPL2 in one or more estrogen-induced cancer-free reference samples, wherein an elevated level of expression of ALPPL2 in the sample obtained from the subject relative to that in one or more reference samples is indicative of an increased risk of the subject developing an estrogen-induced cancer.

Typically, the elevated level of expression of ALPPL2 positively correlates with estrogen levels.

In another aspect, the present disclosure provides a method for determining or predicting prognosis for a subject with an estrogen-induced cancer, the method comprising executing the steps of:
- (a) determining the level of expression of ALPPL2 in a biological sample obtained from the subject;
- (b) comparing the determined level of expression to the level of expression of ALPPL2 in one or more estrogen-induced cancer-free reference samples; and
- (c) determining or predicting prognosis for the subject based on the determined level of expression and said comparison.

In an embodiment predicting prognosis comprises predicting subject survival.

Also provided herein are kits for use in detecting and screening for estrogen-induced cancer, wherein the kits comprise one or more reagents for determining the expression of ALPPL2 as defined in the above embodiments.

Also provided herein is a computer system or apparatus, configured to aid in the detection or diagnosis of estrogen-induced cancer, the risk of a subject developing said cancer, or the prognosis of a subject having said cancer, wherein computer software is employed to analyze data relating to the expression of ALPPL2 as defined in the above embodiments, and to provide a diagnostic, risk assessment or prognostic prediction with respect to a subject. Typically, the computational software is also employed to compare said data to data relating to the expression of ALPPL2 in one or more cancer-free reference samples.

A further aspect of the present disclosure provides a method for selecting a subject for treatment for an estrogen-induced cancer, the method comprising:
- (a) executing a step of determining the level of expression of ALPPL2 as defined in the above embodiments in a biological sample derived from a subject, wherein the level of expression of the ALPPL2 relative to the level of expression of ALPPL2 in one or more estrogen-induced cancer-free reference samples is indicative of the presence of an estrogen-induced cancer in the subject; and
- (b) selecting a subject, identified in (a) as having an estrogen-induced cancer, for treatment for said cancer.

A further aspect of the present disclosure provides a method for monitoring the response of a subject to a therapeutic treatment for an estrogen-induced cancer, the method comprising:
- (a) obtaining from a subject a first biological sample, wherein the first biological sample is obtained before or after commencement of therapeutic treatment;
- (b) executing the step of determining the level of expression of ALPPL2 as defined in the above embodiments in the first biological sample;
- (c) obtaining from the subject a second biological sample, wherein the second biological sample is obtained at a time point after commencement of therapeutic treatment and after the first biological sample is obtained;
- (d) executing the step of determining the level of expression of ALPPL2 as defined in the above embodiments in the second biological sample; and
- (e) comparing the level of expression of the ALPPL2 in the first and second biological samples, wherein a change in the level of expression between the first and second biological samples is indicative of whether or not the subject is responding to the therapeutic treatment.

The method may further comprise obtaining and executing steps in respect of a third or subsequent sample. Typically, the first, second and any subsequent samples are of the same body fluid.

A further aspect of the present disclosure provides a protocol for monitoring the efficacy of a therapeutic treatment for an estrogen-induced cancer, the protocol comprising:
- (a) obtaining from a subject a first biological sample, wherein the first biological sample is obtained before or after commencement of therapeutic treatment;
- (b) executing the step of determining the level of expression of ALPPL2 as defined in the above embodiments in the first biological sample;
- (c) obtaining from the subject a second biological sample, wherein the second biological sample is obtained at a time point after commencement of therapeutic treatment and after the first biological sample is obtained;
- (d) executing the step of determining the level of expression of ALPPL2 as defined in the above embodiments in the second biological sample; and
- (e) comparing the level of expression of the ALPPL2 in the first and second biological samples, wherein a change in the level of expression between the first and second biological samples is indicative of whether or not the therapeutic treatment is effective.

The protocol may further comprise obtaining and executing steps in respect of a third or subsequent sample. Typically, the first, second and any subsequent samples are of the same body fluid.

The above described protocol may also be used in the screening of candidate agents for treating the estrogen-induced cancer.

BRIEF DESCRIPTION OF THE DRAWINGS

Embodiments of the disclosure are described herein, by way of non-limiting example only, with reference to the following drawings.

DETAILED DESCRIPTION

Figure 1:
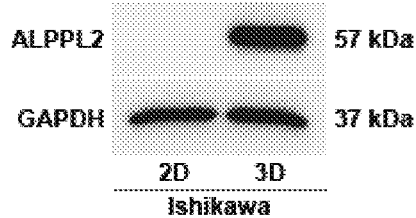
FIG. 1. Immunoblot for ALPPL2 protein in 2D and 3D culture of Ishikawa cells.

Unless defined otherwise, all technical and scientific terms used herein have the same meaning as is commonly understood by one of skill in the art to which the disclosure belongs.

As used herein, the singular forms "a", "an" and "the" also include plural aspects (i.e. at least one or more than one) unless the context clearly dictates otherwise. Thus, for example, reference to "a miRNA" includes a single miRNA, as well as two or more miRNAs.

In the context of this specification, the term "about," is understood to refer to a range of numbers that a person of skill in the art would consider equivalent to the recited value in the context of achieving the same function or result.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

"ALPPL2" refers to the placental-like alkaline phosphatase 2 protein. This term may also be used herein, depending on the context, to refer to the gene, cDNA sequence or mRNA sequence encoding the ALPPL2 protein. Human ALPPL2 is a 533 amino acid membrane bound glycosylated enzyme, including a 19 amino acid N-terminal signal peptide. When present at elevated levels, ALPPL2 is secreted from cells. Whilst the present disclosure typically refers to the protein and gene as found in humans, those skilled in the art will appreciate that homologues of the human sequence from other species are also contemplated and encompassed. The cDNA encoding human ALPPL2 is located in the National Center for Biotechnology Information (NCBI) database as Accession No. NM_031313. An exemplary amino acid sequence of the human ALPPL2 protein, encompassing the N-terminal signal peptide is set forth in SEQ ID NO: 1. An exemplary amino acid sequence of the mature human ALPPL2 protein (minus the N-terminal signal peptide) is set forth in SEQ ID NO: 2. An exemplary nucleotide sequence of the human ALPPL2 gene is set forth in SEQ ID NO:3.

The term "expression" is used herein in its broadest context to denote a measurable (qualitatively or quantitatively measurable) presence of a gene or protein. As described hereinbelow, a variety of methods of determining or measuring expression of ALPPL2 are contemplated. In some embodiments, measuring the expression of ALPPL2 comprises determining the level of the protein or mRNA. As used herein the terms "level" and "amount" may be used interchangeably to refer to a quantitative amount, a semi-quantitative amount, a relative amount, a concentration, or the like. Thus, these terms encompass absolute or relative amounts or concentrations of a protein or mRNA in a sample, including levels in a population of subjects represented as mean levels and standard deviations.

As used herein, the term "derived from" means originates from or obtained from. The terms "derived from" and "obtained from" may be used interchangeably herein.

The term "subject" as used herein refers to mammals and includes humans, primates, livestock animals (e.g. sheep, pigs, cattle, horses, donkeys), laboratory test animals (eg. mice, rabbits, rats, guinea pigs), companion animals (eg. dogs, cats) and captive wild animals (eg. foxes, kangaroos, deer). Typically, the mammal is human or a laboratory test animal. More typically, the mammal is a human.

The present inventors investigated the secretome of endometrial cancer cells. Specifically, the transcriptome of endometrial cancer organoids was analysed, and ALPPL2 (Alkaline Phosphatase, Placental-Like 2) was identified as the most significant, highly secreted protein from endometrial cancer organoids. The inventors have found a significant positive correlation between estrogen levels and ALPPL2 expression, both in vitro and in vivo. ALPPL2 is shown to be overexpressed in both tissue and plasma samples from endometrial cancer patients, and tissue samples from human ovarian cancer patients. Overexpression of ALPPL2 is also shown to be associated with a poor survival rate in endometrial cancer patients. The surprising findings of the present study, exemplified herein, reveal that ALPPL2 is a useful biomarker for endometrial and ovarian cancer, for use in blood-based (for example blood plasma-based) diagnosis and prognosis of endometrial and ovarian cancer. ALPPL2 displays significantly improved diagnostic and prognostic potential than CA-125.

Accordingly, one aspect of the present disclosure provides a method for detecting an estrogen-induced cancer in a subject, comprising executing the steps of:
  (a) determining the level of expression of placental-like alkaline phosphatase 2 (ALPPL2) in a biological sample obtained from the subject; and
  (b) comparing the determined level of expression to the level of expression of ALPPL2 in one or more estrogen-induced cancer-free reference samples,
wherein an elevated level of expression of ALPPL2 in the sample obtained from the subject relative to that in one or more reference samples is indicative of the presence of estrogen-induced cancer in the subject.

Another aspect of the present disclosure provides a method for identifying a subject at risk of developing an estrogen-induced cancer, the method comprising the steps of:
  (a) determining the level of expression of ALPPL2 in a biological sample obtained from the subject; and
  (b) comparing the determined level of expression to the level of expression of ALPPL2 in one or more estrogen-induced cancer-free reference samples,
wherein an elevated level of expression of ALPPL2 in the sample obtained from the subject relative to that in one or more reference samples is indicative of an increased risk of the subject developing an estrogen-induced cancer.

Another aspect of the present disclosure provides a method for determining or predicting prognosis for a subject with an estrogen-induced cancer, the method comprising executing the steps of:
  (a) determining the level of expression of ALPPL2 in a biological sample obtained from the subject;
  (b) comparing the determined level of expression to the level of expression of ALPPL2 in one or more estrogen-induced cancer-free reference samples; and
  (c) determining or predicting prognosis for the subject based on the determined level of expression and said comparison.

Embodiments of the present disclosure provide a biomarker suitable for the rapid and early detection and diagnosis of estrogen-induced cancers, thereby enabling appropriate treatment and patient management strategies to be put into place before progression of the disease to later stages less amenable to treatment. The present disclosure thereby also provides means of improving the prognosis of sufferers of such cancer by early intervention facilitated by the employment of ALPPL2 as a biomarker.

In the context of the present specification, the term "estrogen-induced cancer" refers to a cancer associated with estrogen production and activity. Typically, an "estrogen-induced cancer" is one in which estrogen is implicated in the etiology of, and is associated with increased risk of, the cancer. The terms "estrogen-associated" and "estrogen-related" may be used interchangeably with "estrogen-induced". Examples of estrogen-induced cancers include endometrial (uterine) cancer, ovarian cancer and breast cancer.

In particular embodiments of the present disclosure, the estrogen-induced cancer may be endometrial (uterine) cancer or ovarian cancer. Typically the cancer is a carcinoma. Other exemplary forms of endometrial or ovarian cancer which may be diagnosed in accordance with the present disclosure include sarcomas and carcinosarcomas.

Biological samples used to determine expression levels of ALPPL2 may be derived from any suitable body fluid or tissue. For example the sample may comprise blood (such as erythrocytes, leukocytes, whole blood, blood plasma or blood serum), saliva, sputum, urine, breath, condensed breath, or tissue. Where the sample comprises tissue, typically the tissue is tissue affected by the estrogen-induced cancer. In a particular embodiment the sample comprises whole blood, blood plasma or blood serum. It is within the skill and capability of those of ordinary skill in the art to determine suitable biological samples that may be obtained from subjects for use in the methods of the present disclosure.

The biological sample may be processed and analyzed for the purpose of determining the presence of cancer in accordance with the present disclosure, almost immediately following collection (i.e., as a fresh sample), or it may be stored for subsequent analysis. If storage of the biological sample is desired or required, it would be understood by persons skilled in the art that it should ideally be stored under conditions that preserve the integrity of the biomarker within the sample (e.g., at −80° C.).

It will be understood by those skilled in the art that the method of determining or measuring expression of ALPPL2 in a biological sample can be quantitative, semi-quantitative or qualitative in nature. For example, quantitative analyses may provide an amount or concentration of ALPPL2 in the sample within an appropriate error margin (e.g., mean+/−standard deviation). By contrast, semi-quantitative or qualitative analyses will typically provide an indication of the relative amount of ALPPL2 in a sample. This may involve a comparison of an amount of ALPPL2 in a first sample with an amount of ALPPL2 in a second sample, and making a determination as to the relative amount between the first and second samples.

Any suitable method or technique may be used to measure or determine ALPPL2 expression in accordance with the present disclosure. The skilled addressee will appreciate that the present disclosure is not limited by reference to the means by which ALPPL2 expression is determined and/or quantified. The skilled addressee will be able determine the appropriate means of detecting or measuring expression in any given circumstance without undue burden or experimentation or the need for further invention.

Exemplary methods for determining expression of ALPPL2 at the protein or polypeptide level include, for example, immunoassay using an antibody(ies) that bind with the ALPPL2 protein such as enzyme-linked immunosorbent assay (ELISA) or immunoblotting, 2D-gel electrophoresis (including 2D-DIGE), multiplex protein expression assays, western blotting, immunoprecipitation assays, HPLC, LC/MS, flow cytometry, column chromatography and spectral analysis including, for example, mass spectroscopy, magnetic resonance imaging (MM) spectroscopy, and single photon emission computed tomography (SPECT).

Exemplary methods for determining expression of ALPPL2 at the mRNA level include PCR, RNA and cDNA microarrays, ligase chain reaction, oligonucleotide ligation assay, next generation sequencing, gel electrophoresis, northern blotting, flow cytometry and in situ hybridisation. Exemplary PCR methods include, but are not limited to, reverse transcriptase PCR, real time PCR, quantitative PCR (qPCR), quantitative real time PCR (qRT-PCR), and multiplex PCR.

By way of example only, particles (e.g. beads) in suspension or in planar arrays can be used as the basis of assays for the determination of protein or mRNA expression. For example, biomolecules such as antibodies or oligonucleotides can be conjugated to the surface of beads to bind and capture ALPPL2 protein or mRNA, respectively. A range of detection methods, such as flow cytometric or other suitable imaging technologies, known to persons skilled in the art can then be used for characterization of the beads and detection of protein or mRNA presence.

For the purposes of the present methods, the expression levels of ALPPL2 are typically compared to reference levels, where the reference levels represent the absence of the estrogen-induced cancer. The reference levels may be from one or more reference samples. In this context the term "reference" or "reference sample" means one or more biological samples from individuals or groups of individuals diagnosed as not having estrogen-induced cancer. Alternatively or in addition, there may be circumstances in which it is desirable to compare levels of ALPPL2 expression from a subject under evaluation with one or more reference samples, where the reference sample means one or more biological samples from individuals or groups of individuals with a confirmed diagnosis of estrogen-induced cancer. In such cases, the confirmed diagnosis may include a confirmed diagnosis of a specific stage or grade of the estrogen-induced cancer.

A "reference sample" may comprise the compilation of data from one or more individuals whose diagnosis as a "reference" or "control" for the purposes of the present disclosure has been confirmed. That is, samples to be used as reference samples or controls need not be specifically or immediately obtained for the purpose of comparison with the sample(s) obtained from a subject under assessment.

Thus, reference levels of ALPPL2 expression can be pre-determined using biological samples from a cohort of healthy subjects (i.e. free of estrogen-induced cancer) to obtain an accurate median or mean. Reference levels can be determined for various samples, such as various cell and tissue types and various body fluids. For the most accurate detection, the reference sample used for comparison comprises the same type of sample as taken from the subject under assessment in the provided methods. Reference levels also can be matched by age, sex or other factors.

In accordance with the present disclosure, expression data from one or more samples, including samples under comparison, may be subjected to one or more statistical analyses, thereby facilitating the diagnostic or prognostic method. The statistical analysis may comprise, for example, receiver operator characteristic (ROC) analysis, logistic regression analysis including logistical regression with k-fold validation, Spearman's rank correlation analysis, the Mann-Whitney U test, and calculation of Pearson's correlation coefficient (PCC) values.

Methods of the present disclosure may be employed to detect or diagnose cancer in a subject where no diagnosis, or confirmed diagnosis, previously existed. Such diagnosis may be made in the absence of clinical symptoms of the cancer. For example, a subject may present as having an increased risk of, be predisposed to, or otherwise susceptible to, the development of an estrogen-induced cancer, for example as a result of family history, obesity, estrogen exposure, determined estrogen levels, presence of one or more genetic mutations or presence of an underlying disease or condition. By way of example, individuals with Lynch syndrome (hereditary non-polyposis colorectal cancer), typically when linked to germline mutations in a mismatch repair gene (e.g., MLH1, MSH2, MSH6 or PMS2), are at an increased risk of developing endometrial or ovarian cancer. Similarly, individuals with mutations in a BRCA gene are predisposed to breast, ovarian and endometrial cancer. The skilled addressee will appreciate that there are numerous factors, including symptoms, mutations and conditions, that predispose individuals to estrogen-induced cancer, or lead to an increased risk of developing such a cancer, and the scope of the present disclosure is not to be limited by reference to any one factor.

Alternatively the methods disclosed herein may be used to confirm a diagnosis or preliminary diagnosis offered by a different means, for example, ultrasound, tissue biopsy, MRI or PET scan, or a blood test for one or more additional biomarkers associated with the cancer. Thus, the present methods may be used independently, or in conjunction, with one or more other diagnostic or prognostic methods, tests or assays. Diagnoses made in accordance with embodiments disclosed herein may therefore be correlated with other means of diagnosing estrogen-induced cancer.

Kits

All essential materials and reagents required for detecting or measuring for the expression of ALPPL2 may be assembled together in a kit. Thus, the present disclosure provides diagnostic and test kits for detecting or determining the level of expression of ALPPL2 in a biological sample, in order to facilitate the detection or diagnosis of an estrogen-induced cancer, risk of developing such a cancer, or the prognosis of a subject having such a cancer. Kits typically comprise one or more reagents and/or devices for use in performing the methods disclosed herein. For example, the kits may contain reagents for isolating cells or cellular components from biological samples, such as reagents for extracting or isolating RNA or protein, and/or for measuring the expression of ALPPL2 mRNA or protein.

Kits may also include suitable software, or access to suitable software, to facilitate comparisons between reference levels of expression and expression levels from subjects to be analyzed, and to facilitate statistical analysis that may be employed in such comparisons. Accordingly, also provided herein is a computer system or apparatus, configured to aid in the detection or diagnosis of estrogen-induced cancer, risk of developing such a cancer, or the prognosis of a subject having such a cancer, wherein computer software is employed to analyze data relating to the expression of ALPPL2 as defined herein, and to provide a diagnostic or prognostic prediction with respect to a subject. Typically, the computational software is also employed to compare said data to data relating to the expression of ALPPL2 in one or more estrogen-induced cancer-free reference samples.

Kits may also include suitable means to receive a biological sample, one or more containers or vessels for carrying out methods described herein, positive and negative controls, including a reference sample, and instructions for the use of kit components contained therein, in accordance with the methods disclosed herein.

Therapeutic Regimens

A subject who is identified, in accordance with the methods of the present disclosure described hereinbefore as having an estrogen-induced cancer, can be selected for treatment, or stratified into a treatment group, wherein an appropriate therapeutic regimen can be adopted or prescribed with a view to treating the cancer.

Thus, in an embodiment, the methods disclosed herein may comprise the step of exposing (i.e., subjecting) a subject identified as having an estrogen-induced cancer to a therapeutic regimen for treating said cancer.

A further aspect of the present disclosure provides a method for selecting a subject for treatment for an estrogen-induced cancer, the method comprising:

(a) executing a step of determining the level of expression of ALPPL2 as defined in the above embodiments in a biological sample derived from a subject, wherein the level of expression of the ALPPL2 relative to the level of expression of ALPPL2 in one or more estrogen-induced cancer-free reference samples is indicative of the presence of an estrogen-induced cancer in the subject; and (b) selecting a subject, identified in (a) as having an estrogen-induced cancer, for treatment for said cancer.

The nature of the therapeutic treatment or regimen to be employed can be determined by persons skilled in the art and will typically depend on factors such as, but not limited to, the age, weight and general health of the subject. Suitable therapeutic treatments and regimens would be known to persons skilled in the art, non-limiting examples of which include surgery, chemotherapy and/or radiotherapy.

As used herein the terms "treating" and "treatment" refer to any and all uses which remedy the cancer, or otherwise prevent, hinder, retard, or reverse the progression of the cancer or one or more symptoms thereof in any way whatsoever. Thus the term "treating" and the like are to be considered in their broadest context. For example, treatment does not necessarily imply that a patient is treated until total recovery. In conditions which display or a characterized by multiple symptoms, the treatment or prevention need not necessarily remedy, prevent, hinder, retard, or reverse all of said symptoms, but may prevent, hinder, retard, or reverse one or more of said symptoms.

Without being bound by theory or a particular mode of practice, it also follows from the present disclosure that the methods disclosed herein can be used to monitor the response of a subject to a therapeutic treatment, and monitor the efficacy of a therapeutic treatment, for an estrogen-induced cancer, whereby the expression of ALPPL2 is determined (e.g., measured) in biological samples obtained from a subject at two or more separate time points, including for example before commencement of treatment, during the course of treatment and after cessation of treatment, to determine whether the subject is adequately responding to the treatment, and whether the treatment is effective, for example, in inhibiting the development or progression of the cancer.

Accordingly, an aspect of the present disclosure provides a method for monitoring the response of a subject to a therapeutic treatment for an estrogen-induced cancer, the method comprising:

(a) obtaining from a subject a first biological sample, wherein the first biological sample is obtained before or after commencement of therapeutic treatment;

(b) executing the step of determining the level of expression of ALPPL2 as defined in the above embodiments in the first biological sample;

(c) obtaining from the subject a second biological sample, wherein the second biological sample is obtained at a time point after commencement of therapeutic treatment and after the first biological sample is obtained;

(d) executing the step of determining the level of expression of ALPPL2 as defined in the above embodiments in the second biological sample; and (e) comparing the level of expression of the ALPPL2 in the first and second biological samples, wherein a change in the level of expression between the first and second biological samples is indicative of whether or not the subject is responding to the therapeutic treatment.

The present disclosure also provides a protocol for monitoring the efficacy of a therapeutic treatment for an estrogen-induced cancer, the protocol comprising:

(a) obtaining from a subject a first biological sample, wherein the first biological sample is obtained before or after commencement of therapeutic treatment;

(b) executing the step of determining the level of expression of ALPPL2 as defined in the above embodiments in the first biological sample;

(c) obtaining from the subject a second biological sample, wherein the second biological sample is obtained at a time point after commencement of therapeutic treatment and after the first biological sample is obtained;

(d) executing the step of determining the level of expression of ALPPL2 as defined in the above embodiments in the second biological sample; and (e) comparing the level of expression of the ALPPL2 in the first and second biological samples, wherein a change in the level of expression between the first and second biological samples is indicative of whether or not the therapeutic treatment is effective.

The method or protocol may further comprise obtaining and executing steps in respect of a third or subsequent sample. Typically, the first, second and any subsequent samples are of the same body fluid.

In an embodiment, a change of expression of ALPPL2 between the first and second (or subsequent) sample may be indicative of an effective therapeutic regimen. Where the protocol disclosed herein indicates that the therapeutic regimen is ineffective (i.e. no change in expression of ALPPL2 between the first and second, or subsequent, sample), the protocol may further comprise altering or otherwise modifying the therapeutic regimen with a view to providing a more efficacious or aggressive treatment. This may comprise administering to the subject additional doses of the same agent with which they are being treated or changing the dose and/or type of medication.

Also provided herein are screening methods for candidate compounds and compositions as therapeutic agents to treat estrogen-induced cancer. For example, a suitable therapeutic agent may be obtained by selecting a compound or composition capable of modulating the expression level of ALPPL2. Such methods of screening for a therapeutic agent can be carried out either in vivo or in vitro. For example, a screening method may be performed by administering a candidate compound or composition to a subject, such as a laboratory test animal subject; measuring the expression level of ALPPL2 in a biological sample from the subject; and selecting a compound or composition that increases or decreases the expression level of ALPPL2, as compared to that in a control with which the candidate compound or composition has not been contacted.

Methods for selecting a compound or composition for treating an estrogen-induced cancer, for monitoring the efficacy of such a treatment or for screening candidate agents may also be employed by, for example: obtaining a biological sample from a subject, such as a laboratory test animal subject; separately maintaining aliquots of the sample in the presence of a plurality of compounds or compositions; comparing expression of ALPPL2 in each of the aliquots; and selecting one of the compounds or compositions which significantly alters the level of expression of ALPPL2 in the aliquot containing that compound or composition, relative to the levels of expression of ALPPL2 in the presence of other compounds or compositions.

It will be appreciated that the above described terms and associated definitions are used for the purpose of explanation only and are not intended to be limiting.

In order that the invention may be readily understood and put into practical effect, particular preferred embodiments will now be described by way of the following non-limiting examples.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

EXAMPLES

Example 1—Experimental Procedures

Cell Lines and Culture Conditions

The human endometrial adenocarcinoma cell line Ishikawa (Sigma #99040201) was cultured in MEM (HyClone) medium supplemented with 5% heat-inactivated FBS (Bovogen Biologicals), 2 mmol/L L-glutamine (HyClone), and antibiotics (50 U/mL penicillin, 50 mg/L streptomycin; Gibco) in a humidified atmosphere at 37° C. containing 5% $CO_2$. Cell line authentication was done by short tandem repeat (STR) DNA profiling method and *mycoplasma* contamination in cells was routinely conducted using MycoAlert™ Plus *Mycoplasma* detection kit (Lonza).

Clinical Samples

Human Endometrial Cancer Patient Samples:

Human endometrial cancer and adjacent normal tissue samples were collected from patients undergoing tumor resection or surgical debulking at John Hunter Hospital using a protocol approved by the University of Newcastle Human Research Ethics Committee. Fresh tissue samples were transported to the laboratory, washed with phosphate buffered saline (PBS) and fixed in 10% buffered formalin for paraffin embedding and sectioning. Corresponding normal adjacent and tumor sections were also flash frozen and stored in liquid nitrogen for protein isolation and western blot analysis.

Human Plasma Samples:

The University of Newcastle Human Research Ethics Committee approved the protocol to collect human plasma sample. Blood plasma samples from normal and endometrial adenocarcinoma patients were collected from Victorian Cancer Biobank, Australia.

Tissue Microarrays:

Endometrial cancer tissue microarray (EMC1021, US Biomax) including 97 cases of carcinoma (Grade 1, 2, and 3) and 5 normal sections was immunohistochemically analyzed for ALPPL2 protein expression. Quantification of ALPPL2 staining intensities was performed using the Halo™ image analysis platform; H-scores were calculated and used to establish the receiver-operating characteristic (ROC) curve between normal and adenocarcinoma cases.

TCGA Data:

The association between ALPPL2 or MUC16 expression and patient survival was validated using a uterine cancer data set from TCGA (Cancer Genome Atlas: www.cancergenome.nih.gov). The TCGA microarray gene expression data was used to calculate the ALPPL2 or MUC16 mRNA expression z-scores for 548 tumor samples. A z-score of ±2 was used as a cutoff for to classify the samples into high and low ALPPL2 or MUC16 expression groups. The overall and disease-free Kaplan-Meier survival analysis for these two groups of patients were performed using the cBioPortal for Cancer Genomics (Cerami et al, *Cancer Discov*, 2012, 2:401-4).

Animals and Hormone Treatments

The University of Newcastle Animal Care and Ethics Committee approved all procedures for mice experimentation. To study the effect of steroid hormones, 8- to 12-week-old female C57BL/6 mice were ovariectomized and allowed to rest for seven days. One week post-ovariectomy, mice were subcutaneously implanted with hormone pellets of 17-β-oestradiol (0.72 mg per pellet, 90 days release, n=3) or 17-β-oestradiol and progesterone (0.72 mg and 100 mg per pellet respectively, 90 days release, n=3, Innovative Research of America). Mice with subcutaneous incision but no pellet were used as controls (Sham, n=3). After 3 months, uterine tissues were collected, processed for formalin-fixed paraffin-embedding (FFPE) and snap frozen for protein or RNA isolation.

RNA-Seq and Data Analysis

Total RNA was isolated from 2D monolayer and 3D grown Ishikawa organoids using RNeasy Mini kit (Qiagen) following manufacturer's instructions. Library preparation, sequencing, and analysis of read counts were performed as described previously (Sahoo et al, *Oncotarget*, 2017, 8:71400-17). Transcripts with generalized log 2 fold change (GFOLD) value greater than 2 were considered statistically significant (Feng et al, *Bioinformatics*, 2012, 28: 2782-8).

3D Organoid Formation Assay and Immunofluorescence Staining 5,000 Ishikawa cells/well were seeded in triplicate in 100 μL medium onto 96-well tissue culture plates coated with a thin layer of reduced growth factor basement membrane extract (Cultrex® RGF BME: Trevigen) and were allowed to form organoids. After 24 hours, the organoids were subjected to desired hormonal treatments: 10 nmol/L estrogen ((β-Estradiol, Sigma #E8875) and 100 nmol/L progesterone (Medroxyprogesterone 17-acetate, Sigma #M1629). The culture medium containing desired hormone concentration was changed on every 48 hours. On day 7, colony size was measured and images were photographed using JuLI™ Stage Real-Time Cell History Recorder (NanoEnTek) in an incubator at 37° C. humidified with 5% $CO_2$. 72 hours post-treatment, cells were incubated with CellTiter-Glo® 3D Reagent (Promega) for 30 minutes at room temperature and luminescence signal was recorded using the FLUOstar OPTIMA (BMG Labtech). Ishikawa 3D organoids were fixed in 4% paraformaldehyde (Electron Microscopy Sciences, ProSciTech) for 20 minutes and processed for immunofluorescence, as described previously (Sahoo et al, *Oncotarget*, 2017, 8:71400-17).

Immunoblotting

Endometrial Cancer Samples:

Human endometrial cancer samples, mouse uterine tissue, and Ishikawa cells were lysed in ice-cold RIPA (radioimmunoprecipitation assay) buffer (50 mmol/L Tris-HCl pH 7.5, 150 mmol/L NaCl, 1% NP-40, 0.5% Sodium deoxycholate, 0.1% SDS) containing protease and phosphatase inhibitors (Sigma). The lysates were centrifuged at 12,000 rpm for 10 minutes at 4° C. and supernatant was collected. Aliquots of purified lysates containing equal protein mass were boiled in 1× Laemmli sample buffer (0.04 mol/L Tris-HCl pH 6.8, 0.2% SDS, 0.01% bromophenol blue, 10% β-mercaptoethanol and 10% glycerol) for 5 minutes at 95°

C. and resolved by 10% SDS-PAGE gels. The protein bands were electrophoretically transferred to nitrocellulose blotting membranes (GE Healthcare Life Sciences), blocked in TBS-T (0.1% Tween 20 in TBS) containing 5% skim milk (w/v) for 1 hour at room temperature and probed with primary antibody ALPPL2 (1:500 dilution, Santa Cruz Biotechnology #sc-134255) for overnight incubation at 4° C. The membrane was washed and incubated with secondary horseradish peroxidase-conjugated anti-mouse antibody (Jackson ImmunoResearch Laboratories) for 1 hour at room temperature. The membrane was washed again in TBS-T, developed using a chemiluminescent substrate (Millipore) for detection of HRP and the protein bands were detected by chemiluminescence (Fujifilm LAS-4000). GAPDH was used as a loading control. Densitometric quantification was performed using ImageJ software (NIH, USA).

Ovarian Cancer Samples:

Human ovarian cancer samples were lysed in ice-cold RIPA (radioimmunoprecipitation assay) buffer (50 mmol/L Tris-HCl pH 7.5, 150 mmol/L NaCl, 1% NP-40, 0.5% Sodium deoxycholate, 0.1% SDS) containing protease and phosphatase inhibitors (Sigma). The lysates were centrifuged at 12,000 rpm for 10 minutes at 4° C. and supernatant was collected. Aliquots of purified lysates containing equal protein mass were boiled in 1× Laemmli sample buffer (0.04 mol/L Tris-HCl pH 6.8, 0.2% SDS, 0.01% bromophenol blue, 10% β-mercaptoethanol and 10% glycerol) for 5 minutes at 95° C. and resolved by 10% SDS-PAGE gels. The protein bands were electrophoretically transferred to nitrocellulose blotting membranes (GE Healthcare Life Sciences), blocked in TBS-T (0.1% Tween 20 in TBS) containing 5% skim milk (w/v) for 1 hour at room temperature and probed with primary antibody ALPPL2 (1:500 dilution, Santa Cruz Biotechnology #sc-134255) for overnight incubation at 4° C. The membrane was washed and incubated with secondary horseradish peroxidase-conjugated anti-mouse antibody (Jackson ImmunoResearch Laboratories) for 1 hour at room temperature. The membrane was washed again in TBS-T, developed using a chemiluminescent substrate (Millipore) for detection of HRP and the protein bands were detected by chemiluminescence (Fujifilm LAS-4000). GAPDH was used as a loading control. Densitometric quantification was performed using ImageJ software (NIH, USA).

Histology, Immunohistochemistry (IHC) and Digital Quantification

For histological analyses, human endometrial cancer tissue and mouse uteri were fixed in 10% neutral buffered formalin solution overnight at 4° C. and transferred to 70% ethanol until further processing. Formalin-fixed tissues were processed, embedded in paraffin wax and sectioned at 5 μm thickness. Haematoxylin and eosin staining and immunohistochemistry were performed using standard protocols as described previously (Sahoo et al, *Mol Cancer Res*, 2018 16(2):309-321). Tissue sections were incubated with primary antibody ALPPL2 (1:50 dilution, Santa Cruz Biotechnology #sc-134255) for overnight at 4° C., followed by peroxidase-conjugated secondary antibodies (Thermo Fisher Scientific) and DAB substrate (Sigma) to detect bound antibodies. Tissues were counterstained with hematoxylin to visualize cellular morphology. Images were captured using an Aperio AT2 slide scanner (Leica Biosystems, Victoria, Australia) with same gain and exposure time. Quantitative IHC analysis was performed using the Halo™ image analysis platform and the pixel intensities of DAB staining were calculated using the Area Quantification v1.0 algorithm (Indica Labs, New Mexico, USA). Immunohistochemistry intensity score (H-Score) was calculated from pixel intensity values (the sum of 3×% of pixels with strong staining+2×% of pixels with moderate staining+1×% pixels with weak staining).

RNA Extraction, Synthesis of First Strand cDNA and qRT-PCR

Total RNA was isolated from estrogen or progesterone treated mouse uterus and Ishikawa cells using RNeasy Mini kit (Qiagen) following manufacturer's instructions. 250 ng of total RNA was used for the synthesis of cDNA using $RT^2$ First Strand Kit (Qiagen). The cDNA was amplified using sequence-specific Alppl2 primers. Quantitative real-time PCR (Q-PCR) was performed using $RT^2$ SYBR Green ROX qPCR Mastermix (Qiagen) on a 7900 HT FAST Thermocycler (Applied Biosystems) through a pre-incubation step, and 40 amplification cycles (including denaturation, annealing and extension segments). Relative quantification [comparative Ct ($2^{-\Delta\Delta ct}$) method] was used to compare the expression level of the target gene with the housekeeping gene (Gapdh) in different treatment groups. Primer sequences were: human ALPPL2 (F: 5' TGT-TACCGAGAGCGAGAGC 3' (SEQ ID NO:4), R: 5' GTGGGTCTCTCCGTCCAG 3' (SEQ ID NO: 5)), mouse Alppl2 (F: 5' ACACATGGCTCTGTCCAAGA 3' (SEQ ID NO: 6), R: 5' TCGTGTTGCACTGGTTGAAG 3' (SEQ ID NO: 7)), human GAPDH (F: 5' GCCACATCGCTCA-GACACCAT 3' (SEQ ID NO: 8), R: 5' GAAGGGGTCAT-TGATGGCAA 3' (SEQ ID NO: 9)) and mouse Gapdh (F: 5' TGGCAAAGTGGAGATTGTTGCC 3' (SEQ ID NO: 10), R: 5' AAGATGGTGATGGGCTTCCCG 3' (SEQ ID NO: 11)).

ELISA

Plasma ALPPL2 and CA-125 level in normal and endometrial adenocarcinoma patients were analyzed using human ALPPL2 (CUSABIO Life science #CSB-EL001633HU) and CA-125 (Abcam #ab195213) ELISA kit following the manufacturer's instructions. Briefly, the assay plate was incubated with standards and samples. Following incubation, the plate was incubated with biotin and HRP-avidin labeled antibody for 1 hour. After washing, the plate was developed with a colorimetric reagent and read at 450 nm wavelength.

Statistical Analysis

Statistical analysis was performed with GraphPad Prism 7.02 software. All in vitro experiments were repeated thrice with three biological replicates per repeat and the data were expressed as the mean±SEM. Statistical analyses were performed by the Student's t-test (unpaired, two-tailed). ALPPL2 and CA-125 protein levels were compared across groups using the Mann-Whitney test. The Chi-square or Fisher's exact test was used for categorical data. Differences between overall and disease-free survival were estimated using Kaplan-Meier analysis and log-rank test. The prognostic power of ALPPL2 and CA-125 biomarker was compared using the area under the receiver-operating characteristic curve (AUC); AUC=0 means extremely unlikely to happen in clinical practice, values close to 0.5 indicates the discrimination of performance close to chance while AUC=1 means the diagnostic test is perfect in the differentiation between the disease and normal. A P value<0.05 was considered statistically significant.

Example 2—ALPPL2 as a Secretory Protein in Human Endometrial Cancer Organoids

To identify a potential tumor biomarker for diagnosis of endometrial cancer patients, the inventors characterized the secretome of endometrial cancer cells. To characterize the secretome of human endometrial cancer cells, the inventors cultured Ishikawa cells in three-dimension (3D) on an extracellular matrix substratum to form organoids. In contrast to conventional two-dimensional culture, the culture of organoids is beneficial as they are self-organizing, stable and resemble the tissue of origin. The endometrial organoids imitate in vivo uterine glands, respond to steroid signaling and secrete components of 'uterine milk'.

Endometrial cancer organoids formed in 3D were typically initiated from a single cell to organize into a relevant multicellular polarized (shown by GM130 on the apical side) and glandular (shown by actin filaments arrangement) architecture. In a 3D environment by acquiring a native glandular pattern, endometrial cancer cells turn secretory in nature and synthesized a greater number of secretory proteins compared to other proteins (nuclear, cytoplasmic and membranous) (data not shown). Ttranscriptome analysis of Ishikawa organoids identified 111 secreted protein-coding genes (90 upregulated, 21 downregulated) compared to the monolayer of Ishikawa cells (>2-fold change, P<0.05). Further cumulative analysis of all the highly significant (GFOLD>2; P<0.05; eFDR, 1) transcripts revealed ALPPL2 as the most abundantly secreted protein-coding gene (~80-fold) in Ishikawa organoids. ALPPL2 expression was validated at the translational level using immunoblots and showed distinct expression in Ishikawa organoids, in concordant with RNA-seq data (FIG. 1). These results suggest that endometrial cancer cells secrete ALPPL2 abundantly in their native state.

Figure 2:
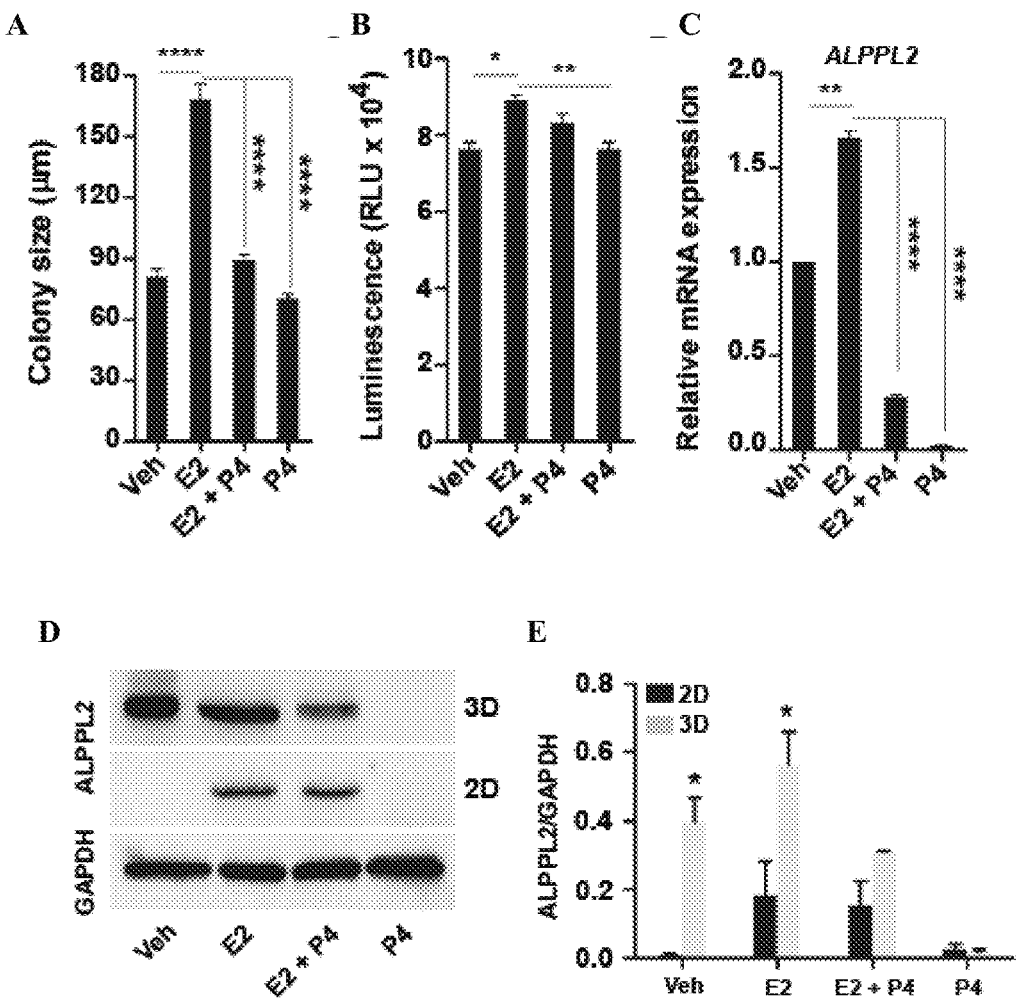
FIG. 2. Ishikawa cells were grown in 3D and treated with estrogen (E2, 10 nmol/L) and progesterone (P4, 100 nmol/L). (A) The bar graph shows average colony size from different treatment groups (n=3). The diameter of 50 colonies from each treatment group was analyzed. (B) Ishikawa cells were treated with E2 and P4 and assayed for proliferation (n=3). (C) Quantitative real-time PCR analysis of ALPPL2 mRNA expression levels on cDNA from Ishikawa organoids dosed with E2 and/or P4 (n=3). (D) Immunoblot analysis of ALPPL2 protein from Ishikawa cells in 2D and 3D environment under different treatment condition (n=3). (E) Densitometric quantification of the western blots in panel E. Scale bar, 100 μm. The results represent the mean±SEM; *, $P<0.05$; , $P<0.01$; **, $P<0.0001$.

Example 3—Endometrial Cancer Organoid Growth and ALPPL2 Expression Show Similar Trend Towards Estrogen and Progesterone The inventors demonstrate here that size and proliferation of Ishikawa organoids increased upon estrogen (E2) administration and the mitogenic action of E2 was counterbalanced by progesterone (P4) (FIGS. 2A and 2B). As endometrial cancer cells secrete ALPPL2, the inventors questioned whether E2 mediated endometrial cancer cell proliferation also stimulates ALPPL2 expression. Quantitative real-time PCR analysis of ALPPL2 was performed in Ishikawa organoids grown in E2 alone, P4 alone or in E2 and P4. ALPPL2 mRNA expression was significantly upregulated in E2 treated organoids whereas P4 inhibited this effect (FIG. 2C). Overexpression of ALPPL2 was also confirmed by western blot analysis on total cell lysate of Ishikawa cells and organoids treated with E2 and/or P4 (FIGS. 2D and 2E). The results concluded that E2 promotes Ishikawa organoid proliferation with elevated ALPPL2 expression.

Figure 3:
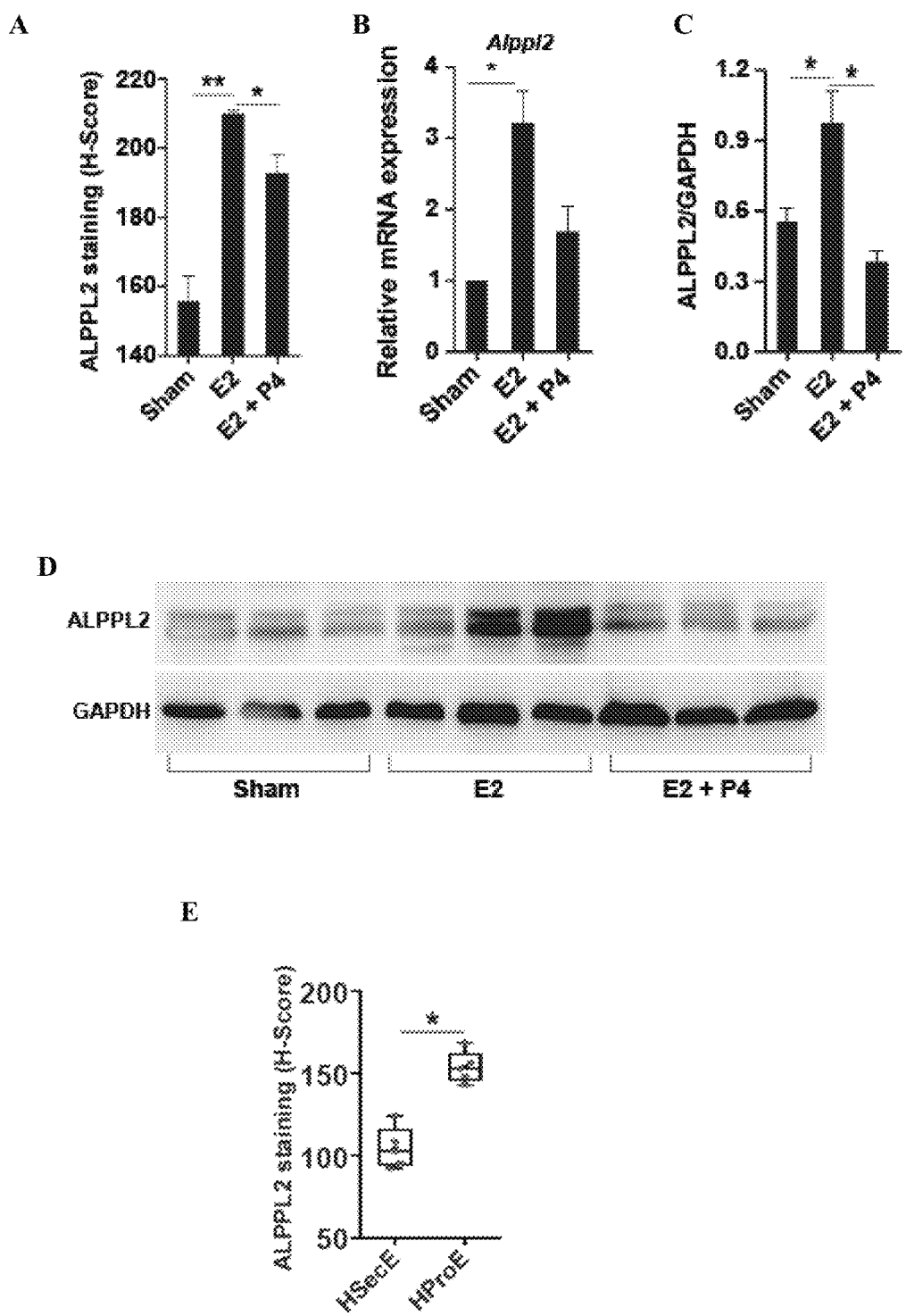
FIG. 3. (A) The graph shows quantification of ALPPL2 staining intensity (n=3). (B) Alppl2 mRNA expression levels on cDNA from E2 and P4 treated mouse uterus (n=3). (C) Western blot of protein lysate from E2 and P4 treated mice uteri was analyzed for ALPPL2 (n=3 mice/group). (D) Densitometric quantification of ALPPL2 western blot bands is shown as a bar graph (n=3). (E) ALPPL2 staining intensity was quantified by H-score and shown as a bar graph (n=5). HSecE, human secretory endometrium; HProE, human proliferative endometrium. Scale bar, 100 μm. The results represent the mean±SEM; *, $P<0.05$; **, $P<0.01$.

Example 4—Steroid Hormones Regulate ALPPL2 Expression in Mouse and Human Uterus To validate response of ALPPL2 to steroid hormones in vivo, wild-type C57BL/6 mice were ovariectomized and treated with vehicle, E2 or E2 and P4 for 3 months (n=3 per treatment). Effect of steroid hormones on mice uteri was confirmed by histological analysis, which showed increased endometrial hyperplasia in E2 treated group compared to E2 and P4 treated uteri (data not shown). Immunohistochemical analysis showed an increase in ALPPL2 expression in E2 treated mice whereas in E2 and P4 treated mice, P4 attenuated the effect of E2 (FIG. 3A). The expression of ALPPL2 in E2 and/or P4 treated mice uterus was also ascertained at mRNA and protein level (FIG. 3B-3D). ALPPL2 protein expression was also investigated during proliferative (E2 response) and secretory phase (P4 response) of the menstrual cycle. Human secretory endometrium displayed modest ALPPL2 expression compared to the proliferative endometrium (FIG. 3E). Taken together, these results demonstrate that ALPPL2 is an E2 responsive gene and hyperestrogenic state of the uterus can be detected by ALPPL2 expression level.

Example 5—Prognostic Significance of ALPPL2 in Endometrial Adenocarcinoma

Figure 4:
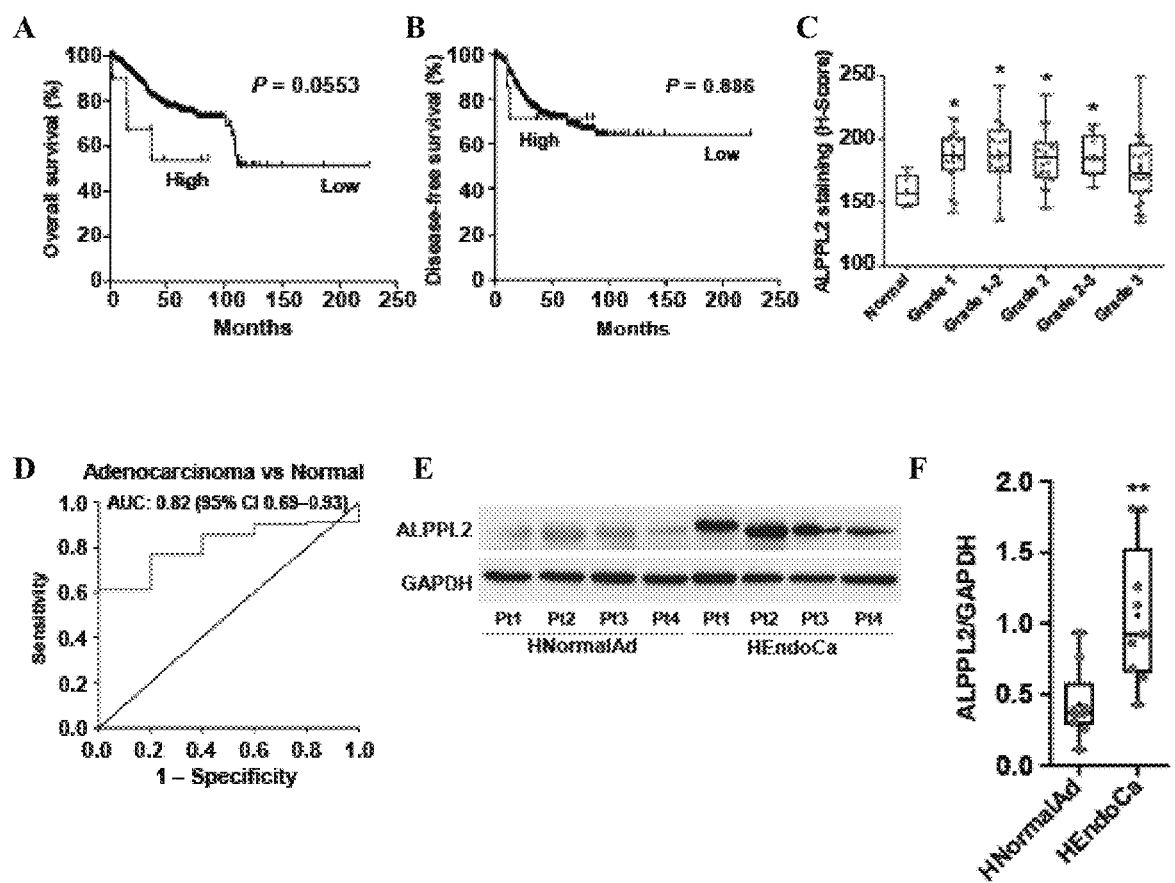
FIG. 4. (A) Overall and (B) Disease-free Kaplan-Meier analysis of ALPPL2 expression in patients with endometrial cancer (TCGA Project). The analysis was done by median cut with the P value of the log-rank test. Black lines, samples with low ALPPL2; red lines, samples with high ALPPL2. (C) Quantification of ALPPL2 staining intensities is shown as H-Score in normal (n=5), grade 1 (n=16), grade 1-2 (n=22), grade 2 (n=20), grade 2-3 (n=9) and grade 3 (n=25) endometrial cancer patients. Whisker box plot represents medians with minimum and maximum values. P value was determined by Mann-Whitney U tests as compared to normal cases. (D) Shown is a ROC curve for ALPPL2 expression levels in endometrioid adenocarcinomas versus normal cases. (E) Western blot of protein lysate from cancerous and normal adjacent uterine tissue was analyzed for ALPPL2 expression (n=9 patients per group). Representative western blot of normal and cancerous tissue from four patients is shown. (F) Densitometric quantification of the bands in F was performed, averaged and shown as a whisker box plot (n=9). Pt, patient; AUC, area under the ROC curve; CI, confidence interval; HNormalAd, normal adjacent human endometrium; HEndoCa, human endometrial cancer. Scale bar, 100 μm. The results represent the mean±SEM; *, $P<0.05$; **, $P<0.01$.

The positive correlation between sex-steroid hormones and endometrial cancer has been described within the framework of the 'unopposed estrogen hypothesis', which implicates that women with high endogenous estrogen level are at increased risk of developing endometrial cancer. In the present study, the inventors found that ALPPL2 expression positively correlates with an increase in E2 concentration. To evaluate the relevance of these findings in a clinical cohort, publicly available RNA-seq gene expression data from the TCGA (The Cancer Genome Atlas) uterine corpus endometrial carcinoma subset was analyzed. TCGA data analysis revealed amplification of ALPPL2 is strongly associated with poor outcome in endometrial cancer patients. Kaplan-Meier analysis of 548 samples with median cut and log-rank test showed a significant difference in overall (Cox hazard ratio of 0.2183, 95% CI: 0.0458-1.041, P=0.0139) and disease-free (Cox hazard ratio of 0.8976, 95% CI: 0.2062-3.908, P=0.5067) survival time, linking ALPPL2 with poor prognosis (FIGS. 4A and 4B). Those patients with high ALPPL2 expression were found to have decreased overall survival (36% deceased) compared to patients with low ALPPL2 expression (16% deceased).

To test the prognostic value of ALPPL2 protein levels in endometrial cancer patients, immunohistochemistry was performed on a formalin-fixed, paraffin-embedded (FFPE) tissue microarray consisting of 61 low-grade and 30 high-grade endometrial adenocarcinomas (Table 1).

TABLE 1

Association of clinicopathologic variables with ALPPL2 expression in patients with endometrial cancer

| Clinical parameters in cancers | ALPPL2 expression | | P value |
| --- | --- | --- | --- |
| | Low | High | |
| Histology | | | 0.3829 |
| Adenocarcinoma, n = 91 | 45 (49.5%) | 46 (50.5%) | |
| Adenosquamous carcinoma, n = 4 | 2 (50.0%) | 2 (50.0%) | |
| Undifferentiated carcinoma, n = 2 | 0 | 2 | |
| Histopathological grade | | | 0.0632 |
| Low (1 or 2), n = 61 | 26 (42.6%) | 35 (57.4%) | |
| High (3), n = 30 | 19 (63.3%) | 11 (36.7%) | |
| Age (Years) | | | 0.0110 |
| <50, n = 34 | 10 (29.4%) | 24 (70.6%) | |
| ≥50, n = 63 | 36 (57.1%) | 27 (42.9%) | |

The average ALPPL2 protein staining intensity was higher in adenocarcinoma cases compared to the normal endometrium (FIG. 4C; ALPPL2 H-Score: normal, 159±5.83 vs. adenocarcinoma, 180.1±4.37; P=0.0174). In addition, analysis of different grades of adenocarcinomas also demonstrated a significant increase in ALPPL2 protein expression compared to normal (FIG. 4C). The corresponding area under the receiver operating curve (ROC) of normal versus adenocarcinoma patients was 0.82 (95% CI 0.69-0.93, P=0.0197) (FIG. 4D). Furthermore, the inventors compared ALPPL2 expression levels between endometrial cancer tissue and corresponding normal adjacent tissue from the same patient. All the normal adjacent and endometrial cancer tissue sections were histologically analyzed before proceeding to protein isolation. Consistent with tissue microarray data, western blot analysis ascertained significant upregulation of ALPPL2 in endometrial cancer tissue compared to normal adjacent endometrium (FIGS. 4E and 4F). Collectively, these data show that significant upregulation of ALPPL2 protein during endometrial cancer can be utilized for patient prognosis.

TCGA dataset analysis also demonstrated that ALPPL2 is a better predictor of patient survival than CA-125 (MUC16 expression: high, 8.6% deceased vs. low, 17.9% deceased; data not shown). These data suggest ALPPL2 up-regulation is an indicator of poor prognosis in endometrial cancer patients.

Figure 5:
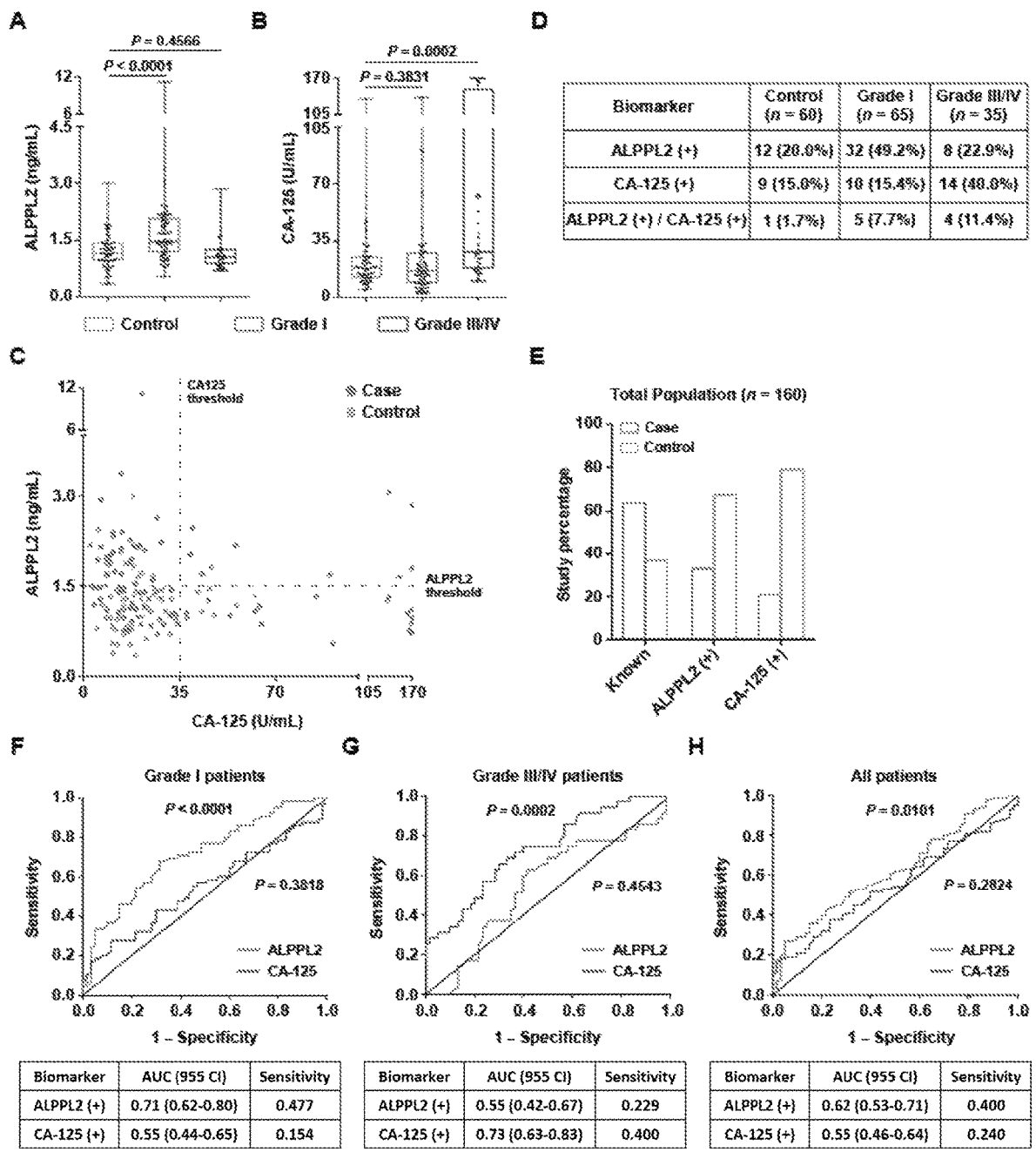
FIG. 5. Whisker box plots show (A) ALPPL2 and (B) CA-125 values in plasma of endometrial cancer patients and normal women. Each box represents maximum, upper quartile, median, lower quartile, and minimum values. (C) Comparison of the discriminatory power of ALPPL2 versus CA-125 for endometrial cancer cases. The vertical line represents the CA-125 threshold (35 U/mL) above which women would be sent to a gynecologist. The horizontal line represents the ALPPL2 threshold, which was selected by taking $75^{th}$ percentile of all control samples and a range between median and $75^{th}$ percentile was considered as borderline. (D) The table displays ALPPL2- and CA-125-positive numbers in case, and control cohorts. (E) The bar graph shows the percentage of total known cases and control samples identified by CA-125 and ALPPL2 biomarker screening. ROC curve analysis of ALPPL2 and CA-125 in grade I (F), grade III/IV (G) and all (H) endometrial cancer case and control groups. AUC, area under the ROC curve; CI, confidence interval.

Example 6—ALPPL2 as a Clinically Useful Blood-Based Tumor Marker for Endometrial Carcinomas ALPPL2 expression was analyzed and compared with CA-125 levels in the plasma of 100 endometrial cancers of various histological types (low- and high-grade) and 60 normal women. Median ALPPL2 levels were significantly higher in grade I endometrial cancer patients (control, 1.172 ng/mL vs. case, 1.486 ng/mL; P<0.0001) whereas patients with advanced stage disease (grade III/IV) displayed higher CA-125 values (control, 18.21 U/mL vs. case, 28.15 U/mL; P=0.0002; FIGS. 5A and 5B). However, overall plasma ALPPL2 levels in patients with endometrial cancer (median, 1.4 ng/mL; range, 0.54-11.12 ng/mL) was significantly higher than normal women (median, 1.1 ng/mL; range, 0.35-2.99 ng/mL; P=0.0101) as compared with CA-125 levels (case: median, 19.48 U/mL; range, 2.59-169.20 U/mL vs. control: 18.21 U/mL; range, 4.84-132.20 U/mL; P=0.2832). The inventors also compared ALPPL2 values with CA-125 values for individual case and control samples (FIG. 5C). With a threshold of 1.5 ng/mL, ALPPL2 was positive in 40 of 100 cases (40%) whereas only 24 of 100 (24%) cases were detected by CA-125 cutoff values (35 U/mL, FIG. 5D). Overall, in a cohort of 160 women, 52 individuals (33%) had higher ALPPL2 threshold values whereas only 33 individuals (12%) had elevated CA-125 values (FIG. 5E). Furthermore, to determine the prognostic significance of ALPPL2, the inventors generated ROC curves to discriminate cancer cases from controls. The superiority of ALPPL2 over CA-125 was strengthened when the analysis was limited to grade I endometrioid endometrial cancer patients (ALPPL2 AUC, 0.71 vs. CA-125 AUC, 0.55; FIG. 5F). Compared with grade I cases, CA-125 displayed better prognosis for grade III/IV patients (CA-125 AUC, 0.73 vs. ALPPL2 AUC, 0.55; FIG. 5G). However, for all patients, the sensitivity of ALPPL2 (0.40) was higher than CA-125 (0.24, FIG. 5H). Thus, it appears that ALPPL2 titers independently better recognize early stage endometrial cancer patients than CA-125.

Example 7—ALPPL2 Expression in Ovarian Cancer

Figure 6:
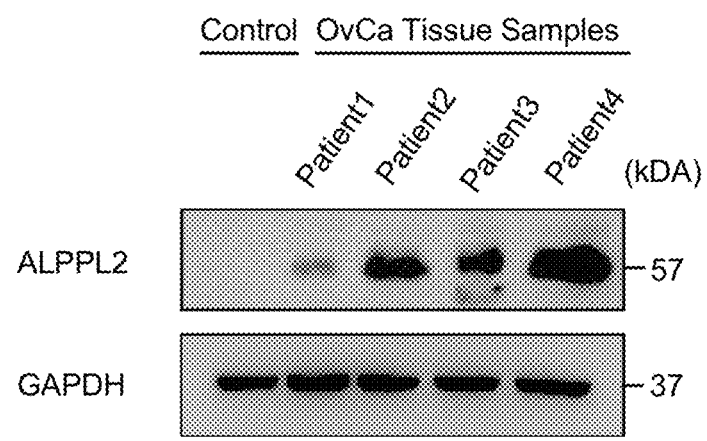
FIG. 6. Imunoblot showing increased expression of ALPPL2 in four ovarian cancer-positive tissue samples compared to a cancer-free negative control.

The inventors then investigated ALPPL2 expression in ovarian tissue samples from four patients with a confirmed diagnosis of ovarian cancer. As shown in FIG. 6, ALPPL2 protein is clearly detectable, and in at least patients 2, 3 and 4 detectable at high levels relative to the housekeeping protein GAPDH, in ovarian cancer tissue samples but not in a control sample from healthy patient without ovarian cancer.

The invention claimed is:

1. A method for treating a subject determined to have an estrogen-induced cancer, the method comprising:
   (a) obtaining or having obtained a biological sample from the subject;
   (b) performing or having performed a biochemical assay on the biological sample to identify the subject as having a level of expression of placental-like alkaline phosphatase 2 (ALPPL2) in the biological sample that is greater than a threshold level from one or more reference samples and is indicative of a presence of the estrogen-induced cancer in the subject; and
   (c) administering a therapy to the subject identified in (b) that is capable of treating the estrogen-induced cancer, wherein the therapy comprises chemotherapy, surgery, or radiotherapy,
   wherein the estrogen-induced cancer is early-stage ovarian cancer or early-stage endometrial cancer.

2. The method according to claim 1, wherein the level of expression of ALPPL2 is a qualitative or quantitative determination of expression of an ALPPL2 protein or of ALPPL2 mRNA.

3. The method according to claim 1, wherein the method further comprises determining a statistical value derived from the level of expression of ALPPL2 from the sample obtained from the subject and the one or more reference samples and comparing said statistical values.

4. The method according to claim 1, wherein the biological sample obtained from the subject is a blood sample.

5. The method according to claim 1, wherein the elevated level of expression of ALPPL2 positively correlates with estrogen levels.

6. The method according to claim 1, wherein the estrogen-induced cancer is stage I ovarian cancer or stage I endometrial cancer.

7. A method for monitoring the response of a subject to a therapeutic treatment for an estrogen-induced cancer, the method comprising:
   (a) obtaining from a subject a first biological sample;
   (b) identifying the subject as having a level of expression of placental-like alkaline phosphatase 2 (ALPPL2) in the first biological sample that is greater than a threshold level;
   (c) selecting a therapy capable of treating an estrogen-induced cancer, wherein the therapy comprises a chemotherapy, a surgery, or radiotherapy;
   (d) administering the selected therapy to the subject;
   (e) obtaining from the subject a second biological sample after (d);
   (f) identifying the subject as having a level of expression of ALPPL2 in the second biological sample that is greater than a threshold level; and
   (g) administering to the subject an additional therapy capable of treating an estrogen-induced cancer, wherein the additional therapy comprises a chemotherapy, a surgery, or radiotherapy,
   wherein the estrogen-induced cancer is early-stage ovarian cancer or early-stage endometrial cancer.

8. The method according to claim 7, further comprising obtaining and executing steps in respect of a third or subsequent sample.

9. The method according to claim 7, wherein the estrogen-induced cancer is stage I ovarian cancer or stage I endometrial cancer.

10. A protocol for monitoring the efficacy of a therapeutic treatment for an estrogen-induced cancer, the protocol comprising:
    (a) obtaining from a subject a first biological sample;
    (b) identifying the subject as having a the-level of expression of placental-like alkaline phosphatase 2 (ALPPL2) in the first biological sample that is greater than a threshold level;
    (c) selecting a first therapy capable of treating an estrogen-induced cancer, wherein the first therapy is a chemotherapy, a surgery, or a radiotherapy;
    (d) administering the selected first therapy to the subject;
    (e) obtaining from the subject a second biological sample after (d);
    (f) determining a level of expression of ALPPL2 in the second biological sample; and
    (g) (i) if the level of expression of ALPPL2 in the second sample is at or greater than the threshold level, then administer a second therapy capable of treating estrogen-induced cancer to the subject, which is a different therapy than the first therapy, wherein the second therapy is a chemotherapy, a surgery, or a radiotherapy; and
    (ii) if the level of expression of ALPPL2 in the second sample is lower than the threshold level and the first therapy is a chemotherapy or a radiotherapy, then maintaining administration of the first therapy,
    wherein the estrogen-induced cancer is early-stage ovarian cancer or early-stage endometrial cancer.

11. The protocol according to claim 10, wherein the estrogen-induced cancer is stage I ovarian cancer or stage I endometrial cancer.

12. The protocol according to claim 10, further comprising obtaining and executing steps in respect of a third or subsequent sample.

* * * * *